United States Patent [19]

Mardiguian

[11] 4,061,777
[45] Dec. 6, 1977

[54] VASODILATORY TERPENO-PHENOXYALKYLAMINES

[75] Inventor: Jean Mardiguian, Paris, France

[73] Assignee: Mar-Pha, Societe d'Etudeet d'Exploitation de Marques Mar-Pha, France

[21] Appl. No.: 566,361

[22] Filed: Apr. 9, 1975

[30] Foreign Application Priority Data

Apr. 11, 1974 United Kingdom ............... 16074/74

[51] Int. Cl.$^2$ ..................... A61K 31/135; C07C 93/06
[52] U.S. Cl. ............................. 424/330; 260/567.6 R; 260/567.6 H; 260/570.7; 424/329
[58] Field of Search ...................... 260/567.6 R, 570.7; 424/330

[56] References Cited

U.S. PATENT DOCUMENTS

| | | | |
|---|---|---|---|
| 3,626,011 | 12/1971 | Bordenca et al. | 260/583 EE |
| 3,639,634 | 2/1972 | Marshall | 424/330 |
| 3,904,622 | 9/1975 | Thominet | 260/247.7 S |
| 3,954,872 | 5/1976 | Köppe et al. | 260/570.7 |

*Primary Examiner*—Leonard Schenkman
*Attorney, Agent, or Firm*—Bucknam and Archer

[57] ABSTRACT

New terpeno-phenoxyalkylamines of the general formula:

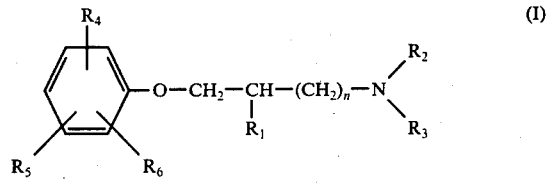

in which $n$ is 0, 1 or 2, $R_1$ is a hydrogen atom, a lower alkyl radical having a straight or branched chain with 1 to 4 carbon atoms, or an OH group, $R_2$ and $R_3$ each represent H, or a lower alkyl radical having a straight chain or branched chain with up to 4 carbon atoms, or a hydroxyethyl radical, $R_4$ is a terpene radical selected from 2-isobornyl, 5-camphyl or 2-norbornyl of exo or endo configuration in the ortho, meta or para position with respect of the ether function $R_5$ and $R_6$ may each be H, a lower alkyl radical having a straight or branched chain with up to 4 carbon atoms or a halogen atom, as well as their physiologically acceptable non-toxic acid salts and their quaternary ammonium salts having antibacterial and cardiovascular vasodilatory properties.

18 Claims, No Drawings

VASODILATORY TERPENO-PHENOXYALKYLAMINES

The present invention relates to new terpeno-phenoxyalkylamines of the general formula:

$$R_4-\text{Ar}(R_5)(R_6)-O-CH_2-CH(R_1)-(CH_2)_n-N(R_2)(R_3) \quad (I)$$

in which $n = 0, 1$ or $2$;

$R_1$ may be H, or a lower alkyl radical having a straight or branched chain with up to 4 carbon atoms, or an OH group, $R_2$ and $R_3$ each represent H or a lower alkyl radical having a straight or branched chain with up to 4 carbon atoms, or a hydroxyethyl radical, $R_4$ is a terpene radical: 2-isobornyl (a), or 5-camphyl (b), or 2-norbornyl (c), of exo or endo configuration, in the ortho, meta or para position with respect to the ether function;

$R_5$ and $R_6$ may each be H or a lower alkyl radical having up to 4 carbon atoms, saturated or unsaturated having a straight or branched chain, or a halogen atom: Cl, Br, I, F.

More particularly:

$R_1$ is H, or OH $n$ is equal to zero or 1

$R_2$ is a hydrogen atom, $R_3$ is a hydrogen atom or isopropyl radical or a hydroxyethyl group — $CH_2CH_2$—OH $R_5$, $R_6$ each represent a hydrogen atom or a halogen atom, in particular Cl, or Br, or a methyl radical, in position 4 or 5 of the phenol ring.

These amino ethers possess, in particular, interesting bacteriostatic and bactericidal properties vis-a-vis Gram + and Gram − bacteria and may be used as anti-infectous agents. They also have vasodilatory and cardiovascular properties. They may be used in the form of bases or salts of physiologically acceptable non-toxic acids or as quaternary ammonium salts.

Advantageously, it is possible to prepare the terpeno-phenoxyalkylamines according to the invention of formula I in which $R_1$ is an OH group and $n$ is equal to 1, by the action of an alkali metal terpenophenate of formula:

$$R_4-\text{Ar}(R_5)(R_6)-OM$$

in which M designates an alkaline metal, in particular sodium and $R_4$, $R_5$, $R_6$ are defined as above, the epichlorohydrin to form the corresponding 1-terpenophenoxy-2,3-epoxypropane $$R_4-\text{Ar}(R_5)(R_6)-O-CH_2-CH-CH_2\backslash O/$$

which is reacted with ammonia in an alcoholic solution or an amine $HNR_2R_3$ to obtain the desired terpeno-phenoxy-alkylamine.

It is possible to prepare terpeno-phenoxyalkylamines of formula I in which $R_1$, $R_2$, $R_3$ are hydrogen atoms, $n$ is equal to zero, by condensation of an alkaline terpenophenate of formula:

$$R_4-\text{Ar}(R_5)(R_6)-OM$$

in which M designates an alkaline metal and $R_4$, $R_5$, $R_6$ are defined as above with the chloroacetonitrile to form the corresponding 2-terpenophenoxy acetonitrile, derivative followed by the reduction of the nitrile function to an amine by diborane or another appropriate reducing agent.

It is possible to prepare terpeno-phenoxyalkylamines of formula I, in which $R_1$ and $R_2$ are hydrogen atoms and $R_3$ is a hydroxyethyl group, by reduction of the corresponding amide.

$$R_4-\text{Ar}(R_5)(R_6)-O-CH_2(CH_2)_n-CO-NH-CH_2CH_2OH$$

in particular by means of a metallic hydride, for example lithium and aluminium hydride.

The following examples are given to illustrate the invention, without limiting the scope thereof.

EXAMPLE 1

2-(2'-isobornyl-4',5'-dimethylphenoxy) ethylamine.

In a 100 cm³ flask fitted with a condenser and a nitrogen feed pipe there is introduced 2.5g (0.01 mole) of 2-isobornyl-4,5-dimethylphenol, 20 cm³ of methylethyl ketone and 1.38g (0.01 mole) of anhydrous potassium carbonate. The reaction mixture is refluxed for 3 hours after vigorous stirring, and then 24 cm³ of a 0.5N solution of chloroacetonitrile in methylethyl ketone containing 1g of potassium iodide are added dropwise. After 22 hours reflux, the mixture is filtered and the solvent evaporated under reduced pressure. The residue is extracted with chloroform, the organic phase washed with water, dried and the solvent evaporated. The residue is taken up with pentane then crystallised in ethanol. 1.5g of 2-(2'-isobornyl-4',5'-dimethylphenoxy) acetonitrile are obtained, which is dissolved in 100 ml of tetrahydrofuran and treated for 1 hour with a stream of diborane. After 24 hours of contact the excess reagent is destroyed with caution, by ethanol and the solvent is removed. The residue is taken up with hydrochloric ether (a solution of hydrochloric acid in ether) then washed with anhydrous ether. By crystallisation in acetone there is obtained 1.2g of pure product as the hydrochloride (m.pt. 174°–176° C).

ANALYTICAL CHARACTERISTICS

| Analysis for $C_{20}H_{32}ClNO$ (M.W. = 337.5) | | | | |
|---|---|---|---|---|
| | C | H | N | Cl |
| Calculated (%) | 71.1 | 9.48 | 4.15 | 10.5 |
| Found (%) | 70.9 | 9.6 | 4.1 | 10.3 |

I.R. SPECTRA

In dispersion in KBr, the following characteristic bands are observed.

| Isobornyl | 2880, | 2950 cm$^{-1}$ |
|---|---|---|
| Aromatic nucleus | 1500, 845 | |
| Combined ether | 1255, | 1100, 1020 |
| —NH$_3^+$ | 3000, | 2500, 2000, 1610, 1510 |

N.M.R. SPECTRA

In deuterated dimethylsulfoxide, with a T.M.S. reference, the following peaks are noted.

| CH$_3$ | bridge head | 0.6 ppm | Singlet |
|---|---|---|---|
| CH$_3$ | geminal | 0.75–0.77 ppm | Singlets |
| CH$_2$ | cyclic | 1.6 ppm | massive |
| CH$_2$ | ethylamino | 3.15 and 4.15 ppm | |
| —NH$_3^+$ | | 7.05 ppm | Singlet |

EXAMPLE 2

2-(2'-isobornyl-4'-bromo-5'-methylphenoxy) ethylamine

In a 250 cm$^3$ flask provided with a nitrogen delivery tube, there is introduced 15.6g (0.048 mole) of 2-isobornyl-4-bromo-5-methylphenol, 90 cm$^3$ of methylethyl ketone and 6.6g (0.048 mole) of anhydrous potassium carbonate. The reaction mixture is heated at reflux for 3 hours with vigorous magnetic stirring then there is added dropwise a 0.5N solution of chloroacetonitrile in methylethyl ketone containing 1g of potassium iodide. After 22 hours reflux the mixture is filtered on a basic alumina column then eluted with 400 cm$^3$ of ether. After evaporation of the solvent, the residue is crystallised in ethanol and there is thus obtained 14.5g of 2-isobornyl-4-bromo-5-methylphenoxy acetonitrile.

A solution of 5g of the preceding product in 50 cm$^3$ of tetrahydrofuran maintained at ambient temperature is treated for 1 hour with a stream of diborane then left for 18 hours. The mixture is then treated, with caution, with 5 cm$^3$ of ethanol, the solvent evaporated and the residue taken up with hydrochloric ether. There is thus obtained 4.5g of pure product in the form of the hydrochloride (m. pt. = 222°–224° C)

ANALYTICAL CHARACTERISTICS

| Analysis for $C_{19}H_{29}NOClBr$ (M.W. = 402.3) | | | | | |
|---|---|---|---|---|---|
| | C | H | N | Cl | Br |
| Calculated (%) | 56.67 | 7.2 | 3.48 | 8.81 | 19.86 |
| Found (%) | 56.4 | 7.0 | 3.6 | 8.7 | 20.1 |

I.R. SPECTRA

In dispersion in KBr, the following characteristic bands are observed.

| Isobornyl | 2880, 2950 cm$^{-1}$ |
|---|---|
| brominated aromatic nucleus | 1500, 845 |
| combined ether | 1250, 1160, 1040 |
| —NH$_3^+$ | 3000, 2500, 2000, 1610, 1490 |

N.M.R. SPECTRA

In deuterated chloroform with a T.M.S. reference, the following peaks are observed:

| CH$_3$ | bridge head | 0.6 ppm | Singlet |
|---|---|---|---|
| CH$_3$ | geminal | 0.78 and 0.80 ppm | Singlets |
| CH$_3$ | aromatic | 2.3 ppm | Singlet |
| CH$_2$ | cyclic | 1.6 ppm | massive |
| CH$_2$ | ethaylamino | 3.3 and 4.15 ppm | |
| —NH$_3^+$ | | 7.35 ppm | Singlet |

EXAMPLE 3

2-(2'-isobornyl-4'-bromophenoxy) ethylamine

In a 500 cm$^3$ flask fitted with a condenser and a nitrogen delivery tube, there is introduced 19g (0.06 mole) of 2-isobornyl-4-bromophenol, 150 cm$^3$ of methylethyl ketone and 12.5g (0.09 mole) of anhydrous potassium carbonate. The mixture is raised to reflux for 3 hours, under vigorous stirring, and then 150 cm$^3$ of a 0.5N solution of chloroacetonitrile in methylethyl ketone containing 1g of potassium iodide are added dropwise. After 22 hours reflux, the mixture is filtered on an alumina column and eluted with 200 cm$^3$ of ether. After evaporation of the solvent, an oil is obtained which, by crystallisation in pentane, gives 19g of 2-isobornyl-4-bromophenoxy acetonitrile. A solution of 18.5g of the preceding product in 200 cm$^3$ of tetrahydrofuran is treated for 1 hour at ambient temperature with a current of diborane. The mixture is left for 18 hours and treated, with caution, with 20 cm$^3$ of ethanol and then concentrated under reduced pressure. The residue is taken up with a 20% solution of hydrochloric acid in ether. After extraction with ether and alkalization there is isolated 14.5g of a product which is transformed to the hydrochloride by hydrochloric ethanol and separated by precipitation with ether. There is thus obtained 13g of pure product (m.pt. 239°–240° C).

ANALYTICAL CHARACTERISTICS

| Analysis for $C_{18}H_{27}NOBrCl$ (M.W. = 388.35) | | | | | |
|---|---|---|---|---|---|
| | C | H | N | Cl | Br |
| Calculated % | 55.6 | 6.95 | 3.61 | 9.13 | 20.57 |
| Found % | 55.3 | 7.05 | 3.5 | 9.2 | 20.4 |

I.R. SPECTRA

In dispersion in KBr, the following characteristic bands are observed:

| | |
|---|---|
| Isobornyl | 2880, 2950 cm$^{-1}$ |
| Aromatic nucleus | 1490, 890, 810 |
| combined ether | 1240, 1040 |
| —NH$_3^+$ | 3000, 2500, 2000, 1600, 1500 |

N.M.R. SPECTRA

In deuterated dimethyl sulfoxide, with a T.M.S. reference, the following peaks are noted:

| | | | |
|---|---|---|---|
| CH$_3$ | bridge head | 0.6 ppm | Singlet |
| CH$_3$ | geminal | 0.78 and 0.80 ppm | Singlets |
| CH$_2$ | cyclic | 1.62 ppm | |
| CH$_2$ | ethylamino | 3.2 and 4.2 ppm | |
| —NH$_3^+$ | | 8.55 ppm | |

EXAMPLE 4

3-(2'-isobornyl-4,5'-dimethylphenoxy)-1-amino propan-2-ol 258g (1 mole) of 2-isobornyl-4,5-dimethylphenol are dissolved in 300 cm$^3$ toluene and 23g sodium are added. The mixture is heated to reflux until hydrogen is no longer evolved and the solvent is then evaporated. The phenate formed is dissolved in 300 cm$^3$ of tetrahydrofuran and 185g (2 moles) of epichlorohydrin are added dropwise and the mixture refluxed for 18 hours. The solvent is evaporated, the residue taken up in ether, the sodium chloride formed is separated and the ether removed. The impure residue is purified on a silica column by elution with a 1:1 benzene: cyclohexane mixture. There is thus obtained, as an oil, 255g of 1-(2'-isobornyl-4,5'-dimethylphenoxy)-2,3-epoxy propane. 33.1g (0.1 mole) of the preceding product are dissolved in a solution of 34g ammonia in 500 cm$^3$ ethanol. After 3 hours of contact, the mixture is evaporated to dryness under reduced pressure and the residual oil dissolved in ether. The ethereal phase is washed with water to neutrality, dried over magnesium sulphate and the ether removed under vacuum. The residue is dissolved in hydrochloric ethanol and the hydrochloride formed is precipitated with ether and crystallised in acetone. There is thus obtained a pure product (m.pt. 280°-282° C).

ANALYTICAL CHARACTERISTICS

| Analysis for C$_{21}$H$_{34}$NO$_2$Cl (M.W. = 367.9) | | | | |
|---|---|---|---|---|
| | C | H | N | Cl |
| Calculated (%) | 68.55 | 9.33 | 3.81 | 9.64 |
| Found (%) | 68.3 | 9.1 | 3.9 | 9.5 |

I.R. SPECTRA

In dispersion in KBr, the following characteristic bands are observed:

| | |
|---|---|
| Isobornyl | 2880 2950 cm$^{-1}$ |
| Aromatic nucleus | 1620, 1510, 850 |
| Combined ether | 1260, 1035 |
| —NH$_3^+$ | 3000, 2000, 1600, 1510 |
| OH | 3400, 1105 |

N.M.R. SPECTRA

In deuterated dimethylsulfoxide, with a T.M.S. reference the following peaks are observed.

| | | | |
|---|---|---|---|
| CH$_3$ | bridge head | 0.55 ppm | Singlet |
| CH$_3$ | geminal | 0.75 ppm | doublet |
| CH$_3$ | aromatic | 2.05 ppm | doublet |
| NH$_3^+$ | | 8.2 ppm | |
| CH$_2$ | | 3 and 4.15 ppm | multiplet |

EXAMPLE 5

3-(2'-isocamphyl-4',5'-dimethylphenoxy)-1-amino propan-2-ol 116g (0.45 mole) of 2-isocamphyl-4,5-dimethylphenol are dissolved in 700 cm$^3$ of toluene and 10.35g of sodium added. The mixture is refluxed until complete dissolution of sodium occurs. After evaporation of the toluene, the phenate formed is dissolved in anhydrous tetrahydrofuran. 74 cm$^3$ (0.9 mole) of epichlorohydrin are added slowly to the solution which is refluxed for 18 hours. The solvent is removed under reduced pressure, the residue is dissolved in ether, the ethereal solution is washed rapidly with water, dried over magnesium sulphate and the ether removed. The residue obtained is dissolved in a 1:1 mixture of benzene-cyclohexane and filtered on a silica column. There is thus obtained, as an oil, 137g of 1-(2'-isocamphyl-4',5'-dimethylphenoxy)-2,3-epoxy propane. A solution of 9.4g of the preceding product in 200 ml of ethanol containing 17g of ammonia is left for 3 days at ambient temperature. After evaporation, the residue is dissolved in ether, the ethereal solution is washed to neutrality and the ether removed under vacuum. The residue is taken up with hydrochloric ether, the solvent evaporated and the residue crystallised in propane. There is thus obtained 5g of pure product as the hydrochloride (m.pt-260°-264° C).

ANALYTICAL CHARACTERISTICS

| Analysis for C$_{21}$H$_{34}$NO$_2$Cl (M.W. = 367.9) | | | | |
|---|---|---|---|---|
| | C | H | N | O | Cl |
| Calculated (%) | 68.55 | 9.33 | 3.81 | 8.70 | 9.64 |
| Found (%) | 68.1 | 9.4 | 3.65 | | 9.8 |

I.R. SPECTRA

In dispersion in KBr, the following characteristic bands are observed.

| | |
|---|---|
| Isocamphyl | 2880, 2950 cm$^{-1}$ |
| Aromatic nycleus | 1620, 1510, 850 |
| Combined ether | 1265, 1100 |
| NH$_3^+$ | 3000, 2660, 2000, 1600, 1510 |
| >CH OH | OH: 3300 CO: 1080 |

N.M.R. SPECTRA

In deuterated chloroform, with a T.M.S. reference the following peaks are observed.

| | | | |
|---|---|---|---|
| Isocamphyl: | CH$_3$ | 0.8 ppm | doublet |
| | CH$_3$ geminal | 1 ppm | Singlet |
| | CH$_2$ ethylamino | 3.4 and 3.95 ppm | multiplets |
| | NH$_3^+$ | 7.05 ppm | |

EXAMPLE 6

3-(2'-isocamphyl-4',5'-dimethylphenoxy)-1-isopropylamino propan-2-ol.

38g of 1-(2'-isocamphyl-4',5'-dimethylphenoxy)-2,3-epoxypropane, prepared as described in Example 5, and 100 cm³ of isopropylamine are placed in contact for a week at ambient temperature. After removal of excess isopropylamine under reduced pressure, the residue is dissolved in ether, the ethereal phase washed with water, dried over magnesium sulphate, filtered and precipitated by addition of gaseous HCl. By crystallisation in acetone there is obtained 23g of the desired product in the form of the pure hydrochloride (m.pt = 172°–174° C).

ANALYTICAL CHARACTERISTICS

| Analysis for $C_{24}H_{40}NO_2Cl$ (M.W. = 410) | | | | |
|---|---|---|---|---|
| | C | H | N | Cl |
| Calculated (%) | 70.3 | 9.76 | 3.42 | 8.06 |
| Found (%) | 70.1 | 9.6 | 3.4 | 7.85 |

I.R. SPECTRA

In dispersion in KBr, the following characteristic bands are observed:

| Isocamphyl | 2880 2950 cm⁻¹ |
|---|---|
| Aromatic nucleus | 1620, 1590, 1510, 845 |
| Combined ether | 1265, 1110, 1040 |
| $NH_2^+$ | 2800, 2540, 2410, 2000 |
| >CH—OH | OH: 3350 CO: 1090 |

N.M.R. SPECTRA

In deuterated chloroform, with a T.M.S. reference, the following peaks are observed:

| Isocamphyl | 0.85 ppm | doublet |
|---|---|---|
| $CH_3$ geminal | 0.85 and 1.05 ppm | Singlets |
| $CH_3$ (isopropyl) | 1.45 ppm | doublet |
| $CH_2$ | 3.3 and 4.05 ppm | multiplets |
| $NH_2^+$ | 7.7 ppm | |

EXAMPLE 7

N-hydroxyethyl-2-(2'-isobornyl-4',5'-dimethylphenoxy) ethylamine.

In a flask fitted with a condenser and a nitrogen delivery tube, there is introduced 0.5g of lithium aluminium hydride and 50 cm³ of anhydrous ether. To the suspension, cooled to 0° C, there is added dropwise, with stirring, a solution of 3.6g (0.01 mole) of N-hydroxyethyl-(2-isobornyl-4,5-dimethylphenoxy) acetamide in 250 cm³ of anhydrous tetrahydrofuran. The mixture is warmed for 3 hours at 60° C and then the excess hydride is destroyed, the mixture acidified, the organic phase is separated and washed with water and dried over magnesium sulphate. After evaporation of the solvent, the oily residue is crystallised in a 7:3 benzene/isopropyl ether mixture. There is thus obtained 2g of pure product as the hydrochloride (m.p − 158° C).

ANALYTICAL CHARACTERISTICS

| Analysis for $C_{22}H_{36}NO_2Cl$ (M.W. = 381.97) | | | | |
|---|---|---|---|---|
| | C | H | N | Cl |
| Calculated (%) | 69.17 | 9.52 | 3.67 | 9.28 |
| Found (%) | 68.8 | 9.4 | 3.7 | 9.4 |

I.R. SPECTRA

In solution in chloroform, the following characteristic bands are observed.

| Isobornyl | 2880, 2950 cm⁻¹ |
|---|---|
| Aromatic nucleus | 1620, 1505, 850 |
| Combined ether | 1255, 1110, 1020 |
| >$NH_2^+$ | 2750, 2500, 1590 |
| —$CH_2$OH | OH: 3350 CO: 1050 |

N.M.R. SPECTRA

| $CH_3$ | bridge head | 0.65 ppm | Singlet |
|---|---|---|---|
| $CH_3$ | geminal | 0.80 and 0.85 ppm | doublets |
| $CH_3$ | aromatic | 2.15 ppm | Singlet |
| $CH_2$ | | 3.3 ppm | Massive |
| $CH_2$ | | 4 and 4.3 ppm | triplet |
| $NH_2^+$ | | 9.3 ppm | |

EXAMPLE 8

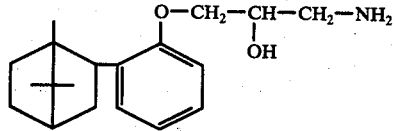

1-Amino 3-(2'-isobornyl phenoxy) propan-2-ol 23g metallic sodium are added to a solution of 23g (0.1 mole) ortho-isobornyl-phenol. The mixture is refluxed in a nitrogen atmosphere until no further hydrogen is evolved, the solvent is removed under reduced pressure and the residue is taken up in 100 cm³ tetrahydrofuran. 18.5g (0.2 mole) epichlorohydrin are added dropwise to the preceding solution, then the mixture is refluxed for 18 hours. After evaporation of the solvent, it is taken up in ether, the ethereal phase is washed in water, dried then the solvent is evaporated. 27g of a yellow/orange oil [1-(2'-isobornyl phenoxy) 2,3-epoxypropane] are obtained, which are dissolved in 400 cm³ methanol saturated with ammonia. After being left for 3 days at ambient temperature, the methanol is removed and the residue is taken up in 500 cm³ hydrochloric ether. The precipitate formed is washed with ether, then crystallised in chlorobenzene. 8g of pure product in the form of the hydrochloride are thus obtained. M.Pt. = 240°–242° C.

ANALYTICAL CHARACTERISTICS

| Analysis for: $C_{19}H_{30}O_2NCl$ (M.W. 339.91) | | | | |
|---|---|---|---|---|
| | C | H | N | Cl |
| Calculated % | 67.14 | 8.90 | 4.12 | 10.43 |
| Found % | 67.22 | 8.95 | 4.20 | 10.53 |

I.R. SPECTRA

In dispersion in KBr the following main bands are noted:

| | |
|---|---|
| Isobornyl | 2950, 2880 cm$^{-1}$; 1475, 1455 cm$^{-1}$ |
| —O—CH$_2$— | 1245 cm$^{-1}$ |
| OH | 3360 cm$^{-1}$ |
| $\overset{\oplus}{N}H_3$ | 3000, 1990 cm$^{-1}$ |

N.M.R. SPECTRA

In solution in D.M.S.O., the following peaks are observed with respect to H.M.D.S. as a reference:

| | | | |
|---|---|---|---|
| Isobornyl | CH$_3$ | bridge head | 0.60 ppm (s) |
| | CH$_3$ | geminal | 0.75 – 0.80 ppm (s) |
| OH | | | 5.75 ppm |
| H aromatic | | | 7 ppm (multiplet) |
| $\overset{\oplus}{N}H_3$ | | | 8.25 ppm |
| —CH$_2$— (lateral chain) | | | 3 – 3.95 ppm |

EXAMPLE 9

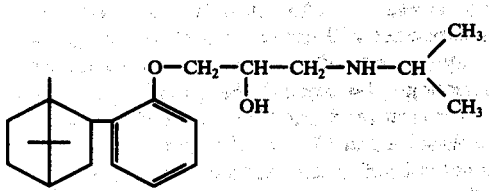

1-Isopropylamino 3-(2'-isobornyl phenoxy) propan-2-ol 28.6g (0.1 mole) of 1-(2'-isobornyl phenoxy) 2,3-epoxypropane, prepared as in Example 8, are dissolved in 150 cm$^3$ isopropylamine. After being left for 3 days at ambient temperature, the excess isopropylamine is removed under vacuum and the residue is taken up in ether. The ethereal phase is washed with water, dried over sodium sulphate and the solvent is evaporated. The residue is taken up in a titrated solution of hydrochloric ethanol. After evaporation, one crystallises from a chloroform-ethanol mixture (5:5) and 24.6g of pure product in the form of the hydrochloride are obtained. M.Pt. 214°–216° C.

ANALYTICAL CHARACTERISTICS

| Analysis for C$_{32}$ H$_{36}$ O$_2$ N Cl (M.W. 382) | | | | |
|---|---|---|---|---|
| | C | H | N | Cl |
| Calculated % | 69.18 | 9.50 | 3.66 | 9.28 |
| Found % | 69.10 | 9.63 | 3.80 | 9.15 |

I.R. SPECTRA

In dispersion in KBr, the following characteristic bands are observed:

| | |
|---|---|
| Isobornyl | 2950, 2875 cm$^{-1}$; 1455, 1475, 1370, 1380 cm$^{-1}$ |
| —O—CH$_2$— | 1240, 1045 cm$^{-1}$ |
| —$\overset{\oplus}{N}H_2$— | 2800 cm$^{-1}$ |
| OH | 3300 cm$^{-1}$ |

N.M.R. SPECTRA

In solution in D.M.S.O. the following peaks are observed with respect to H.M.D.S.:

| | | | |
|---|---|---|---|
| Isobornyl | CH$_3$ | bridge head | 0.68 ppm (s) |
| | CH$_3$ | geminal | 0.72 – 0.75 ppm (s) |
| CH$_3$ | (Isopropyl) | | 1.2 ppm (doublet) |
| CH$_2$ | (lateral chain) | | 3.1 – 3.9 ppm. |
| OH | | | 5.5 ppm |
| >NH$_2$ | | | 9 ppm |
| Aromatic Protons | | | 6.95 ppm (multiplet) |

EXAMPLE 10

2-(2-isobornyl-4-chloro-5-methyl phenoxy) ethylamine 13.9g (0.05 mole) of 2-isobornyl-4-chloro-5-methyl phenol, 150 cm$^3$ methylethyl ketone dried on CaCl$_2$ and 10.4g (0.075 mole) anhydrous potassium carbonate are introduced into a 500 cm$^3$ three necked flask provided with a condenser and supplied with a stream of nitrogen. The mixture is refluxed with stirring for 2 hours, there is then added dropwise 75 cm$^3$ of a normal solution of chloroacetonitrile in methylethyl ketone containing potassium iodide. The latter is heated under reflux for 1 night, then the solvent is evaporated and the residue taken up in cyclohexane at 60° C. After filtration on celite, the solvent is evaporated and the residue crystallised in 25 cm$^3$ heptane. 13.4g of 2-isobornyl-4-chloro-5-methyl phenoxy acetonitrile are thus obtained.

A solution of 12.7g (0.04 mole) of the preceding product in 100 cm$^3$ tetrahydrofuran is subject for 1 hour to mixing with diborane carried along by a nitrogen current. The mixture is then left for 18 hours at ambient temperature. After the addition of ethanol, it is concentrated at reduced pressure and treated with a solution of hydrochloric ether. The precipitate formed is crystallised in acetone. 6g of pure product in the form of the hydrochloride are thus obtained. M.Pt. = 182°–184° C.

ANALYTICAL CHARACTERISTICS

| Analysis for C$_{19}$ H$_{29}$ O N Cl$_2$ (M.W. 358.35) | | | | |
|---|---|---|---|---|
| | C | H | N | Cl |
| Calculated % | 63.68 | 8.16 | 3.91 | 19.79 |
| Found % | 63.75 | 8.10 | 3.80 | 19.91 |

I.R. SPECTRA

In dispersion in KBr, the following main bands are noted:

| | |
|---|---|
| —O—CH$_2$— | 1245 cm$^{-1}$ |
| $\overset{\oplus}{N}H_3$ | 2900, 2020 cm$^{-1}$ |
| Isobornyl | 2950, 2880 cm$^{-1}$ |
| Aromatic nucleus | 1610, 1495 cm$^{-1}$ |

N.M.R. SPECTRA

In solution in CDCl₃, the following peaks are noted with respect to T.M.S. reference:

| Isobornyl | CH₃ | bridge head | 0.62 ppm (s) |
|---|---|---|---|
| | CH₃ | geminal | 0.80 – 0.85 ppm (s) |
| Aromatic nucleus | CH₃ | | 2.28 ppm (s) |
| | | protons | 6.65 – 7.22 ppm (s) |
| CH₂ (lateral chain) | | | 3.3 – 4.12 ppm |
| $\overset{\oplus}{N}H_3$ | | | 7.9 ppm |

EXAMPLE

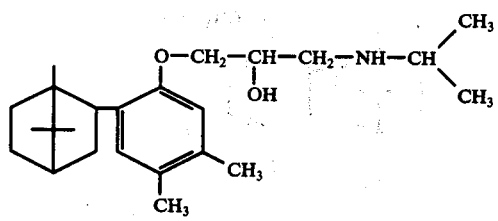

11

1-isopropylamino 3-(2'-isobornyl-4',5'-dimethyl phenoxy) propan-2-ol 20g (0.064 mole) of 1-(2'-isobornyl-4',5'-dimethyl phenoxy) 2,3-epoxypropane, prepared in Example 4, are dissolved in 40 cm³ isopropylamine. After being left at ambient temperature for 7 days, the excess isopropylamine is removed the residue is taken up in ether, the ethereal phase is washed with water, dried and the ether is evaporated. The residual oil is dissolved in 100 cm³ ethanol. 24 cm³ of 3.4N hydrochloric ethanol are added. One precipitates with ether and recrystallises from an ethanol-chloroform mixture (97:3). 17g of pure product in the form of the hydrochloride are thus obtained. M.Pt. = 218°–220° C.

ANALYTICAL CHARACTERISTICS

| Analysis for C₂₄H₄₀O₂N Cl (M.W. 410.04) | | | | |
|---|---|---|---|---|
| | C | H | N | Cl |
| Calculated % | 70.30 | 9.83 | 3.42 | 8.65 |
| Found % | 70.20 | 9.72 | 3.53 | 8.57 |

I.R. SPECTRA

In dispersion in KBr, the following main bands are noted:

| Isobornyl | 2950, 2880 cm⁻¹ |
|---|---|
| —O—CH₂— | 1260, 1110 cm⁻¹ |
| $>\overset{\oplus}{N}H_2$ | 2800, 2530 cm⁻¹ |
| OH | 3350 cm⁻¹ |

N.M.R. SPECTRA

In solution in CDCl₃, the following peaks are observed with respect to the T.M.S. reference:

| Isobornyl | CH₃ | bridge head | 0.7 ppm (s) |
|---|---|---|---|
| | CH₃ | geminal | 0.8 – 0.9 ppm (doublet) |
| Lateral Chain | CH₃ | (isopropyl) | 1.5 ppm |
| | CH₂ | | 3.3 – 4 ppm |
| Aromatic Nucleus | CH₃ | | 2.15 ppm (s) |
| | H | | 6.6 – 7.05 ppm (s) |
| | $>\overset{\oplus}{N}H_2$ | | 7.2 ppm |

EXAMPLE 12

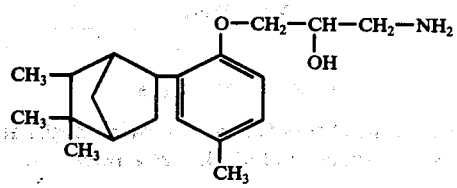

1-amino 3 -(2'-isocamphyl-4'-methyl phenoxy) propan-2-ol 60g (0.245 mole) 2-isocamphyl-4-methyl phenol, 200 cm³ anhydrous toluene and 5.63g (0.245 mole) sodium are introduced into a three-necked flask supplied with a current of nitrogen. The mixture is heated under reflux until no further hydrogen evolves, the solvent is removed and the residue taken up in 200 cm³ anhydrous tetrahydrofuran. 45.4g (0.49 mole) epichlorohydrin are added to the solution obtained, then the mixture is refluxed for 4 hours. After cooling, it is extracted with ether, washed abundantly with water, dried and the ether is evaporated. 60g 1-(2'-isocamphyl-4'-methyl phenoxy) 2,3-epoxypropane are obtained in the form of an oil. 30g(0.1 mole) of this oil are dissolved in 300 cm³ of a solution of ammonia in methanol and left in contact for 1 night. The solvent is then evaporated and the residue taken up in hydrochloric ether. After cooling, 10g of product are obtained in the form of the hydrochloride, which is crystallised in methylethyl ketone. M.Pt. 235°–245° C (dec).

ANALYTICAL CHARACTERISTICS

| Analysis for C₂₀H₃₂O₂N Cl (M.W. 353.93) | | | | |
|---|---|---|---|---|
| | C | H | N | Cl |
| Calculated % | 67.87 | 9.11 | 3.96 | 10.02 |
| Found % | 67.73 | 9.18 | 4.05 | 10.11 |

I.R. SPECTRA

In dispersion in KBr, the following main bands are noted:

| Isocamphyl —O—CH₂— | 2960, 2880; 1480, 1465; 1380, 1370 cm⁻¹ 1245, 1055 cm⁻¹ |
|---|---|
| Aromatic nucleus | 1600, 1510, 810 cm⁻¹ |
| —$\overset{\oplus}{N}H_3$ | 2980, 1990 cm⁻¹ |
| OH | 3380 cm⁻¹ |

N.M.R. SPECTRA

In solution in a D.M.S.O. - CDCl₃ mixture, the following peaks are observed with respect to the T.M.S. reference:

| Isocamphyl | CH₃ | | 0.90 ppm (d) |
|---|---|---|---|
| | CH₃ | geminal | 0.90 – 1.05 ppm (s) |
| CH₂ lateral chain | | | 3.15 – 4 ppm (m) |
| Aromatic protons | | | 6.85 ppm (massive) |

| -continued | |
|---|---|
| $-\overset{\oplus}{N}H_3$ | 8 ppm |

EXAMPLE 13

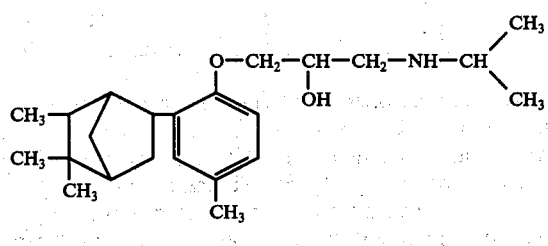

1-isopropylamino 3-(2'-isocamphyl-4'-methyl phenoxy) propan-2-ol

A solution of 30g (0.1 mole) of 1-(2'-isocamphyl-4'-methyl phenoxy) 2,3-epoxypropane, (prepared in example 12) in 150 cm³ isopropylamine is left at ambient temperature for 5 days. The excess amine is then removed and the residue is taken up in ether, the ethereal phase is washed in water, dried and the ether is evaporated. The residue is dissolved in methylethyl ketone. The precipitate formed by bubbling dry hydrochloric acid is re-crystallised from a mixture of methylethyl ketone and methanol. 16g pure product in the form of the hydrochloride are obtained. M.Pt. = 208°–210° C.

ANALYTICAL CHARACTERISTICS

| Analysis for $C_{23}H_{38}O_2NCl$ (M.W. 396.01) | | | | |
|---|---|---|---|---|
| | C | H | N | Cl |
| Calculated % | 69.76 | 9.67 | 3.54 | 8.95 |
| Found % | 69.68 | 9.82 | 3.40 | 9.10 |

I.R. SPECTRA

In dispersion in KBr, the following bands are noted:

| Isocamphyl | 2960, 2870; 1475, 1460 cm⁻¹ |
|---|---|
| —O—CH₂— | 1250, 1065 cm⁻¹ |
| NH₂ | 2800 cm⁻¹ |
| OH | 3350 cm⁻¹ |

N.M.R. SPECTRA

In solution in a mixture of CDCl₃ - D.M.S.O. the following peaks are observed with respect to the T.M.S. reference:

| Isocamphyl | CH₃ | | 0.9 ppm (s) |
|---|---|---|---|
| | CH₃ | geminal | 0.9 - 1.02 ppm (s) |
| Lateral Chain | —CH₂— | | 3.17 - 4 ppm (m) |
| | Isocamphyl (CH₃) | | 1.45 ppm (d) |
| | OH | | 5.9 ppm |
| | $>\overset{\oplus}{N}H_2$ | | 8.9 ppm |
| Aromatic protons | | | 6.85 ppm (m) |

EXAMPLE 14

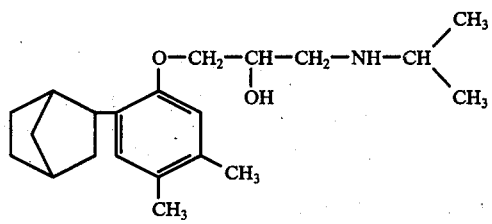

EXAMPLE 14

1-isopropylamino b 3- [2'-(norbornyl)-4',5'-dimethyl phenoxy] propan-2-ol 108g (0.5 mole) of 2-norbornyl-4,5-dimethyl phenol, 600 cm³ anhydrous toluene and 11.5g (0.5 mole) sodium are introduced into a three-necked flask supplied with a nitrogen stream. The reaction mixture is refluxed for 4 hours, the solvent is then removed and the residue taken up in 500 cm³ tetrahydrofuran. 39.4 cm³ (0.5 mole) epichlorohydrin are added and the mixture is heated under reflux for 8 hours. One extracts with ether, washes the ethereal phase with water, dries and evaporates the solvent. 123.6g of 1-(2'-norbornyl-4',5'-dimethyl phenoxy) 2,3-epoxypropane are obtained in the form of oil. 27.2g (0.1 mole) of the preceding product are dissolved in 100 cm³ isopropylamine. After 5 days contact, the excess amine is evaporated under reduced pressure and extracted with ether. After washing with water and drying, the ether is evaporated and the residue taken up in chloroform. One precipitates by adding gaseous hydrochloric acid. By crystallisation in methylethyl ketone, 20g of pure product are obtained. M.Pt. 183°–185° C.

ANALYTICAL CHARACTERISTICS

| Analysis for $C_{21}H_{34}O_2NCl$ (M.W. 367.96) | | | | |
|---|---|---|---|---|
| | C | H | N | Cl |
| Calculated % | 68.55 | 9.31 | 3.81 | 9.63 |
| Found % | 68.67 | 9.20 | 3.90 | 9.57 |

I.R. SPECTRA

In dispersion in KBr, the following main bands are noted:

| Norbornyl | 2950, 2870, 1470, 1460 cm⁻¹ |
|---|---|
| —O—CH₂— | 1270, 1065 cm⁻¹ |
| $>\overset{\oplus}{N}H_2$ | 2800 cm⁻¹ |
| OH | 3420, 3320 cm⁻¹ |
| Aromatic nucleus | 1620, 1590, 856 cm⁻¹ |

N.M.R. SPECTRA

In solution in D.M.S.O., the following peaks are observed with respect to the H.M.D.S. reference:

| Norbornyl | | 1.4 ppm (massive) |
|---|---|---|
| Aromatic nucleus | Protons | 6.65 - 6.80 ppm (s) |
| | CH₃ | 2.1 ppm (s) |
| Lateral Chain | —O—CH₂— | 3.9 ppm (m) |
| | —CH₂— | 3.1 ppm |
| | OH | 6.85 ppm |
| | NH₂ | 9.05 ppm |

| -continued | |
|---|---|
| CH$_3$ (isopropyl) | 1.25 ppm (doublet) |

BACTERIOSTATIC ACTIVITY

The new terpeno-phenoxyalkylamines according to the invention are used particularly as bacteriostatic agents in the treatment of infections by Gram + and Gram bacteria.

The bacteriostatic activity of the products according to the invention have been evaluated by the method of streaks in gelose media. This method comprises making increasing dilutions of the product to be tested, in nutritive gels poured in a Petri dish.

The bacteria to be studied are introduced onto the geloses in parallel streaks by means of a platinum loop which has been immersed in a 24 hour old culture of the bacteria.

The bacteriostatic amount corresponds to the weakest concentration for which the bacteria does not develop along the length of the striations.

The activity of the compounds has been studied vis a vis gram + ve (*Staphylococcus aureus*) and gram − ve (*Escherichia coli*) bacteria.

The table below shows the minimum inhibitory concentrations, expressed in mg/1 of the products of the examples.

|  | Minimum inhibitory concentration (mg/liter) | |
|---|---|---|
|  | *Staphylococcus aureus* | *Escherichia coli* |
| Product of Example 1 | 5 | 7.5 |
| 2 | 5 | 10 |
| 3 | 7.5 | 5 |
| 4 | 5 | 5 |
| 5 | 5 | 5 |
| 6 | 5 |  |
| 7 | 10 | 30 |
| 8 | 20 | 7.5 |
| 10 | 7.5 | 7.5 |
| 12 | 7.5 | 5 |

CORONARO-DILATORY EFFECTS

They were measured in vitro on a heart taken from a rabbit, according to Langendorff's technique. The terpenophenoxy alkylamines according to the invention are administered to the aortic canal at a constant volume of 1 cm$^3$ for 1 minute.

The following table indicates the increase in the coronary output and the duration of this variation, depending on the doses.

| Product of Example | DOSE μg/cm$^3$ | Coronary output | |
|---|---|---|---|
|  |  | Variations in % | Duration in mins. |
| 1 | 3 | + 37 | 5 |
|  | 10 | + 55 | 5 |
| 2 | 1 | + 23 | >15 |
|  | 3 | + 39 | >15 |
| 3 | 1 | + 4 | 3 |
|  | 3 | + 36 | >15 |
| 4 | 3 | +127 | 15 |
|  | 10 | +140 | 12 |
| 5 | 1 | + 13 | 2 |
|  | 3 | + 70 | >15 |
| 6 | 3 | + 36 | 15 |
|  | 10 | + 66 | 9 |
| 7 | 3 | + 51 | >15 |
|  | 10 | +109 | >15 |
| 8 | 3 | + 24 | 6 |
|  | 10 | + 63 | 12 |
| 9 | 3 | + 95 | 4 |

| Product of Example | DOSE μg/cm$^3$ | Coronary output | |
|---|---|---|---|
|  |  | Variations in % | Duration in mins. |
|  | 10 | +102 | 4 |
| 10 | 1 | + 34 | >15 |
|  | 3 | + 60 | >15 |
| 11 | 3 | + 72 | 5 |
|  | 10 | +210 | 12 |
| 12 | 100 | + 31 | 4 |

The terpeno-phenoxyalkylamines according to the invention may be used as vaso-dilatory or cardio-vascular anti-infectious agents. To this end, they may be made in an appropriate form for administration orally, for example tablets capsules etc. containing 50 mg – 200 mg of active ingredient and the dose to be administered is 100 mg to 1000 mg of active ingredient per day.

What is claimed is:

1. A terpeno-phenoxyalkylamine of the general formula:

$$\text{(I)}$$

in which n is 0, 1 or 2,

R$_1$ is a hydrogen atom, a lower alkyl radical having a straight or branched chain with 1 to 4 carbon atoms, or an OH group, R$_2$ and R$_3$ each represent H, or a lower alkyl radical having a straight chain or branched chain with up to 4 carbon atoms, or a hydroxyethyl radical, R$_4$ is a terpene radical chosen from the following group:

2-isobornyl (2)

5-camphyl (5)

or 2-norbornyl (2)

of exo or endo configuration, in the ortho, meta or para position with respect to the ether function, R$_5$ and R$_6$ may each be H, a lower alkyl radical having a straight or branched chain with up to 4 carbon atoms or a halogen atom, or a physiologically acceptable non-toxic acid salt or quaternary ammonium salt thereof.

2. A terpeno-phenoxyalkylamine according to claim 1, characterised in that:

R$_1$ is H or OH n is equal to zero or 1

R$_2$ is a hydrogen atom,

R$_3$ is a hydrogen atom or an isopropyl radical, or a hydroxyethyl group (- CH$_2$CH$_2$-OH).

$R_5$, $R_6$ each represent a hydrogen atom or a halogen atom, or a methyl radical in position 4 or 5 of the phenol ring.

3. 2-(2'-isobornyl-4',5'-dimethyl phenoxy) ethylamine in the form of a base of a physiologically acceptable non-toxic acid salt, or quaternary ammonium salt thereof.

4. 2-(2'-isobornyl-4'-bromo-5'-methyl phenoxy) ethylamine in the form of a base or a physiologically acceptable non-toxic acid salt or quaternary ammonium salt thereof.

5. 2-(2'-isobornyl-4'-bromo phenoxy) ethylamine in the form of a base or a physiologically acceptable non-toxic acid salt or quaternary ammonium salt thereof.

6. 3-(2'-isobornyl-4',5'-dimethyl phenoxy) 1-amino propan-2-ol in the form of a base or a physiologically acceptable non-toxic acid salt or quaternary ammonium salt thereof.

7. 3-(2'-isocamphyl-4',5'-dimethyl phenoxy) 1-amino propan 2-ol in the form of a base or a physiologically acceptable non-toxic acid salt or quaternary ammonium salt thereof.

8. 3-(2'-isocamphyl-4',5'-dimethyl phenoxy) 1-isopropylamino propan 2-ol in the form of a base or a physiologically acceptable non-toxic acid salt or quaternary ammonium salt thereof.

9. N-hydroxyethyl 2-(2'-isobornyl-4',5'-dimethyl phenoxy) ethylamine in the form of a base or a physiologically acceptable non-toxic acid salt or quaternary ammonium salt thereof.

10. 1-amino 3-(2'-isobornyl phenoxy) propan-2-ol in the form of a base of a physiologically acceptable non-toxic acid salt or quaternary ammonium salt thereof.

11. 1-isopropyl amino 3-(2'-isobornyl phenoxy) propan-2-olin the form of a base of a physiologically acceptable non-toxic acid salt or quaternary ammonium salt thereof.

12. 2-(2-isobornyl-4-chloro-5-methyl phenoxy) ethylamine in the form of a base or a physiologically acceptable non-toxic acid salt or quaternary ammonium salt thereof.

13. 1-isopropylamino 3-(2'-isobornyl-4',5' dimethyl phenoxy propan-2-ol in the form of a base or a physiologically acceptable non-toxic acid salt or quaternary ammonium salt thereof.

14. 1-Amino 3-(2-isocamphyl-4'-methyl phenoxy) propan-2-ol in the form of a base or a physiologically acceptable non-toxic acid salt or quaternary ammonium salt thereof.

15. 1-isopropylamino 3-(2'-isocamphyl-4'-methyl phenoxy) propan-2-ol in the form of a base or a physiologically acceptable non-toxic acid salt or quaternary ammonium salt thereof.

16. 1-isopropylamino 3-[2'-norbornyl-4',5'-dimethyl phenoxy] propan-2-ol in the form of a base or a physiologically acceptable non-toxic acid salt or quaternary ammonium salt thereof.

17. A pharmaceutical composition useful for causing vaso-dilatation of the coronaries in a patient containing as the active agent a terpeno-phenoxyalkylamine according to claim 1 in a physiologically active amount and a non-toxic pharmaceutically acceptable carrier.

18. A method for causing vaso-dilation of the coronaries in a patient consisting of administering orally to said patient a pharmaceutical composition according to claim 17 in a dose providing 100 to 1000 mg of active ingredients per day.

* * * * *